United States Patent [19]

Mocella

[11] Patent Number: 4,661,463
[45] Date of Patent: Apr. 28, 1987

[54] PREPARATION OF SOLUBLE MOLYBDENUM CATALYSTS FOR EPOXIDATION OF OLEFINS

[75] Inventor: Michael T. Mocella, West Chester, Pa.

[73] Assignee: Atlantic Richfield Company, Los Angeles, Calif.

[21] Appl. No.: 649,571

[22] Filed: Sep. 12, 1984

Related U.S. Application Data

[63] Continuation of Ser. No. 387,319, Jun. 11, 1982, abandoned, which is a continuation-in-part of Ser. No. 227,116, Jan. 21, 1981, abandoned.

[51] Int. Cl.$^4$ .................... B01J 38/68; C07D 301/19
[52] U.S. Cl. ........................................ 502/24; 502/33; 549/529
[58] Field of Search .................... 502/24, 33

[56] References Cited

U.S. PATENT DOCUMENTS

| | | | |
|---|---|---|---|
| 3,434,975 | 3/1969 | Sheng et al. | 549/529 |
| 3,480,563 | 11/1969 | Bonetti et al. | 549/529 |
| 3,819,663 | 6/1974 | Levine | 549/541 |
| 3,887,361 | 6/1975 | Lemke | 549/529 |
| 4,157,346 | 6/1979 | Lines et al. | 549/529 |

FOREIGN PATENT DOCUMENTS

| | | | |
|---|---|---|---|
| 1550166 | 11/1968 | France | 549/529 |
| 1060122 | 2/1967 | United Kingdom | 549/529 |
| 1317480 | 5/1973 | United Kingdom | 549/529 |

*Primary Examiner*—P. E. Konopka
*Attorney, Agent, or Firm*—Michael S. Jarosz

[57] ABSTRACT

The process of regenerating a soluble, stable molybdenum-containing catalyst suitable for epoxidation of olefins with a hydroperoxide which comprises thermally precipitating and separating a molybdenum-containing solid obtained from a spent catalyst stream derived from a molybdenum catalyzed epoxidation of an olefin and solubilizing the precipitated solid by contacting with a liquid composition comprising an admixture of a monohydroxy alcohol, a polyhydroxy alcohol and an organic peroxide or hydroperoxide, said polyhydroxy alcohol being present in an amount of at least about 2 moles per mole or molybdenum to be solubilized.

9 Claims, No Drawings

PREPARATION OF SOLUBLE MOLYBDENUM CATALYSTS FOR EPOXIDATION OF OLEFINS

This application is a continuation of application Ser. No. 387,319, filed June 11, 1982, which is a continuation-in-part of application Ser. No. 227,116 filed Jan. 21, 1981 now abandoned.

BACKGROUND OF THE INVENTION

Oxirane compounds such as ethylene oxide, propylene oxide, and their higher homologs are valuable articles of commerce. One of the most attractive processes for synthesis of those oxirane compounds is described by Kollar in U.S. Pat. No. 3,351,635. According to Kollar, the oxirane compound (e.g., propylene oxide) may be prepared by epoxidation of an olefinically unsaturated compound (e.g., propylene) by use of an organic hydroperoxide and a suitable catalyst such as molybdenum.

During the epoxidation reaction the hydroperoxide is converted almost quantitatively to the corresponding alcohol. That alcohol may be recovered as a coproduct with the oxirane compound. However, it is the oxirane which is of primary concern.

Kollar teaches that oxirane compounds may be prepared from a wide variety of olefins. Lower olefins having three or four carbon atoms in an aliphatic chain are advantageously epoxidized by the process. The class of olefins commonly termed alpha olefins or primary olefins are epoxidized in a particularly efficient manner by the process. It is known to those in the art that primary olefins, e.g., propylene, butene-1, decene-1, hexadecene-1, etc., are much more difficultly epoxidized than other forms of olefins, excluding only ethylene. Other forms of olefins which are much more easily epoxidized are substituted olefins, alkenes with internal unsaturation, cycloalkenes and the like. Kollar teaches that notwithstanding the relative difficulty in epoxidizing primary olefins, epoxidation proceeds more efficiently when molybdenum, titanium or tungsten catalysts are used. Molybdenum is of special interest. Kollar teaches that activity of those metals for epoxidation of primary olefins is surprisingly high and can lead to high selectivity of propylene to propylene oxide. These high selectivities are obtained at high conversions of hydroperoxide (50% or higher) which conversion levels are important for commercial utilization of the technology.

Kollar's epoxidation reaction proceeds under pressure in the liquid state and, accordingly, a liquid solution of the metal catalyst is preferred. Preparation of a suitable catalyst is taught by Sheng et al in U.S. Pat. No. 3,434,975. According to Sheng, the reaction-medium soluble epoxidation catalyst may be prepared by reacting molybdenum metal with an organic hydroperoxide, peracid or hydrogen peroxide in the presence of a saturated alcohol having one to four carbon atoms.

Another molybdenum epoxidation catalyst is described by Bonetti et al in U.S. Pat. No. 3,480,563. Bonetti teaches that molybdenum trioxide may be reacted with a primary saturated acyclic alcohol having 4 to 22 carbon atoms or with a mono- or polyalkylene glycol monoalkyl ether. The reaction involves heating the molybdenum trioxide in the alcohol or ether to produce an organic soluble molybdenum catalyst.

Maurin et al in U.S. Pat. No. 3,822,321 describes oxidizing olefins with a hydroperoxide using a molybdenum catalyst prepared by reacting a molybdenum compound such as molybdic acid or a molybdic salt with a polyalcohol.

A molybdenum catalyzed epoxidation of olefins is described by Lines et al in U.S. Pat. No. 4,157,346. The catalyst is prepared by reacting an oxygen containing molybdenum compound with an amine (or an amine N-oxide) and alkylene glycol.

British Pat. No. 1,060,122 is concerned with an epoxidation reaction employing catalytic quantities of a molybdenum catalyst which is in the form of an inorganic molybdenum compound.

French Pat. No. 1,550,166 discloses that the molybdic acid esters, and especially glycol esters of molybdic acid, provide certain advantages over previously known catalysts to effect epoxidation employing organic hydroperoxides for reaction with olefinic compounds.

In U.S. Pat. No. 3,887,361 Lemke discloses that spent catalyst solutions obtained from the process of epoxidation of olefins with hydroperoxides in the presence of molybdenum may be treated to precipitate and separate dissolved molybdenum. The Lemke process involves mixing spent catalyst solution with 5 to 50 parts by weight of tertiary-butyl alcohol and heating the mixture to between 100° and 300° C. in a closed vessel or under reflux, thereby resulting in precipitation of molybdenum as a finely divided solid. The solid is disclosed to be suitable for recycle into further epoxidation reactions, as such, or optionally, after dissolution in an organic acid or an acid obtained in the "Oxo process" for production of oxygenated organic derivatives. The Lemke solids typically contain about 30 to about 40 percent by weight of molybdenum.

SUMMARY OF THE INVENTION

It has now been discovered that spent soluble molybdenum catalyst can be effectively regenerated in a stable, soluble form and reused in the epoxidation of olefins. In accordance with the present invention, the method of regenerating soluble molybdenum catalyst for epoxidation of olefins with a hydroperoxide comprises thermally precipitating and separating a molybdenum-containing solid from a spent catalyst solution obtained from the molybdenum catalyzed epoxidation of an olefin and solubilizing the precipitated solid by contacting with composition comprising an admixture of a monohydroxy alcohol, a polyhydroxy alcohol and an organic peroxide or hydroperoxide, said polyhydroxy alcohol being present in amount of at least about 2 moles per mole of molybdenum to be solubilized to produce an active, stable molybdenum-containing catalyst solution. As used in the present specification and the annexed claims, the term "stable catalyst solution" is intended to mean a molybdenum-containing solution which will not precipitate an appreciable amount, i.e. less than about 5% of the molybdenum contained in the solution, of molybdenum upon heating to a temperature of about 90° C. over a period of at least four hours.

The present discovery makes it possible to continuously regenerate, recycle and reuse molybdenum catalyst in a continuous process for molybdenum catalyzed epoxidation of olefins with a hydroperoxide by thermally precipitating and separating a molybdenum-containing solid from a spent catalyst solution obtained from a molybdenum catalyzed olefin epoxidation and solubilizing the precipitated solid in a liquid composition comprising an admixture of a monohydroxy alcohol, a polyhydroxy alcohol and an organic peroxide or hydroperoxide, said polyhydroxy alcohol being present in amount of at least about 2 moles per mole of molybdenum to be stabilized by contacting the solid with such composition to produce an active catalyst solution, and adding a catalytic amount of the active solution to a hydroperoxide epoxidation of an olefin.

As used in the present specification and the annexed claims, the term "spent catalyst solution" is intended to mean that fraction of the epoxidation reaction product effluent remaining after removal by a series of fractionation steps, in conventional manner, of unreacted olefin (for example, propylene), alkylene oxide (for example, propylene oxide), and a major portion of the alcohol corresponding to the hydroperoxide (for example, tertiary butyl hydroperoxide) used in the epoxidation reaction which reaction may be according to the procedure of Kollar, the disclosure of which is hereby incorporated by reference. Spent catalyst solution, which may contain molybdenum at levels of up to about 5 percent by weight, contains some alcohol, acids and other low molecular weight oxygenated compounds; said spent catalyst solution is generally not subjected to any chemical treatment before being subjected to the process of the present invention. It is contemplated that spent catalyst solution, as used herein, includes both the distillation bottoms treated in British Patent Specification No. 1,317,480 and the residue obtained from the wiped film evaporation process according to Levine U.S. Pat. No. 3,819,663, the disclosures of which are also hereby incorporated by reference.

Solid precipitates of molybdenum-containing compounds are obtained from spent catalyst solutions by a variety of methods. The present invention relates to a process for dissolving those solids to produce an active, stable, soluble epoxidation catalyst for use in processes such as those taught by Kollar.

Accordingly, the present invention permits substantially complete recycle of catalyst values to the epoxidation zone and avoids the necessity of disposal of spent molybdenum catalyst solutions which is detrimental from both economic and ecological view points. These and other objects of the invention will become apparent from the following description and examples.

DETAILED DESCRIPTION OF THE INVENTION

In general, the molybdenum catalyzed hydroperoxide epoxidation crude reaction product evolving from processes such as described in the aforementioned Kollar patent, is subjected to a series of fractionation steps whereby there are consecutively separated, as distillate, unreacted olefin, alkylene oxide and the alcohol corresponding to the hydroperoxide. The remaining residue, a heavy organic liquid bottoms stream, contains high boiling by-products and dissolved molybdenum catalyst.

This heavy liquid bottom stream from the last of the above-named distillations comprises the spent catalyst solution which serves as a starting material in the process of the present invention. Normally, this stream contains up to about 10 percent by weight of the alcohol corresponding to the hydroperoxide; for purposes of this invention, this alcohol content is not critical and can vary widely. Also contained in said heavy fraction are formic acid, acetic acid, propylene glycol, dipropylene glycol, glycol ethers and water which are impurities formed in small but still significant quantities, usually during the epoxidation. The heavy fraction also contains a molybdenum epoxidation catalyst in the form of an organic complex mixture which is soluble in the said liquid fraction.

As indicated above, this heavy fraction cannot be recycled directly to the epoxidation zone in view of the fact that the impurities contained therein, and most notably the acid impurities, interfere with the epoxidation reaction. The deleterious effect of these acids is particularly pronounced in a continuous system due to a build-up of the concentration of these materials when a direct recycle is employed. Furthermore, partial recycle of the stream to the epoxidation reaction, over a period of time, results in accumulation of residual materials associated with the catalyst which likewise is deleterious to the overall epoxidation reaction. Nor can the heavy stream be directly burned in order to utilize the heat content thereof, since in such an operation the molybdenum is converted to molybdenum trioxide which settles out on surfaces in the furnace interfering with and ultimately interrupting the furnace operation. Environmental disadvantages are also clearly apparent in any such burning operation.

In accordance with the present invention, the spent catalyst solution, i.e, heavy fraction as described above, is subjected to a thermal treatment thereby precipitating a molybdenum-containing solid from said spent catalyst stream and separating the acidic compounds which are deleterious in the epoxidation reaction from the molybdenum-containing precipitated solid. Customary and regular procedures cannot be employed in accomplishing a resolution of this heavy fraction in view of the tendency of the molybdenum-containing residue to cake, coat and plug conventional apparatus. Thereafter, the precipitated solid molybdenum-containing composition is solubilized by contacting with a liquid composition comprising an admixture of a monohydroxy alcohol, a polyhydroxy alcohol and an organic peroxide or hydroperoxide, said polyhydroxy alcohol being present in amount of at least about 2 moles per mole of molybdenum to be solubilized.

As part of the invention, one of several procedures for effecting thermal precipitation of the molybdenum containing solid from spent catalyst solution may be carried out. In the first of these procedures, the process described in Lemke U.S. Pat. No. 3,887,361, referred to above, may be employed; this process comprises heating the spent catalyst solution with from about 5 to 50 percent by weight of tertiary butyl alcohol to a temperature between about 100° C. to 300° C. in a closed vessel or under reflux and thereafter separating the resulting precipitate containing substantially all the molybdenum originally present in the distillation residue. A second procedure for effecting such thermal treatment involves admixing the spent organic catalyst solution with water in an amount between about 0.5 and 10 percent based on the weight of the organic solution and heating the resultant admixture to a temperature in the range of between about 150° C. and 250° C. under pressure sufficient to maintain the admixture in liquid phase and for a time sufficient to precipitate at least a portion of the molybdenum contained in the organic solution as a solid and thereafter separating the precipitated molybdenum-containing solid from the organic solution, as described and claimed in copending application Ser. No. 227,115 of R. B. Poenisch, entitled "Process for the Recovery of Molybdenum from Organic Solutions", filed Jan. 21, 1981 now U.S. Pat. No. 4,485,074, issued Nov. 27, 1984, and in Dugua U.S. Pat. No. 4,317,802, issued Mar. 2, 1982. The disclosures of the Lemke et al and Dugua patents, and of the Poenisch application are hereby incorporated herein by reference.

Another method for separation of molybdenum-containing solid from the spent catalyst solution involves thermal precipitation procedure disclosed and claimed in my copending application Ser. No. 227,114, entitled "Production of a Solid Molybdenum Precipitate from a Spent Molybdenum Epoxidation Catalyst Solution", filed Jan. 21, 1981 now abandoned. This method comprises removing and recovering dissolved molybdenum as a molybdenum-containing solid by admixing the spent catalyst solution with water in an amount sufficient to produce a two-phase system comprising an organic phase and an aqueous phase, heating the resultant aqueous phase which is rich in molybdenum values to precipitate the molybdenum-containing solid and separating the solid.

In accordance with this method, to recover molybdenum from the spent catalyst solution, water is added to the spent catalyst solution with agitation. A sufficient quantity of water to cause formation of a aqueous phase and a distinct organic phase is necessary for this process. A weight ratio of water to spent catalyst solution from 1:4 to 4:1 is sufficient. However the best molybdenum recovery is observed when about equal weights of water and spent catalyst solution are mixed. After the spent catalyst solution has been thoroughly mixed with water, according to this process, molybdenum precipitation is achieved by heating the mixture to a temperature of 120° C. to 225° C. with preferred temperatures being above 150° C. and most preferred temperatures being about 200° C. The heating time required for a substantially complete precipitation of the solid molybdenum compound ranges from 15 minutes to 3 hours and to a considerable extent, is dependent on the precipitation temperature employed with higher temperatures requiring shorter periods of time for precipitation. Sufficient temperatures to effect precipitation within 15 to 60 minutes are preferred. Heating the two phase mixture of water and spent catalyst solution together at the necessary precipitation temperature results in precipitation of high levels of solid molybdenum compounds which may be separated from the remaining liquid by any conventional solids/liquids separating means, for example, by filtration, centrifugation or merely sedimentation, followed by decanting of the supernatant liquid. The solids obtained by this process have not been fully characterized; however, the solids differ from other molybdenum containing solids which have been recovered by prior art processes such as, for example, the Lemke process discussed above.

The solid molybdenum-containing precipitate resulting from any of the aforementioned thermal precipitation procedures may contain up to about 50, and generally, up to about 40 weight percent molybdenum, by weight. Reuse of the molybdenum contained in the solid precipitate resulting from said thermal treatment requires an efficient method to solubilize the molybdenum so that a high quality epoxidation may be achieved. In accordance with another aspect of the process of the present invention, an active stable catalyst solution may be obtained by contacting the solid thermal precipitate with a liquid composition comprising an admixture of a monohydroxy alcohol, a polyhydroxy alcohol and an organic peroxide or hydroperoxide, said polyhydroxy alcohol being present in an amount of at least about 2 moles per mole of molybdenum to be solubilized.

Hence, in accordance with the present invention, it has been surprisingly found that a mixture of organic monohydroxy alcohol and polyhydroxy alcohol has a synergistic effect on solubilizing precipitated molybdenum-containing solids obtained from the aforementioned thermal treatments in the presence of an oxidizing agent to produce a regenerated catalyst. Polyhydroxy alcohol added to monohydroxy alcohol appears to have the effect of stabilizing the molybdenum solution and prevents reprecipitation. As indicated above, it is essential to employ a minimum of at least 2 moles of organic polyhydroxy compound per mole of molybdenum to be solubilized. The molar ratio suggests that the stabilizing effect is achieved by complexing the soluble molybdenum with polyhydroxy alcohol, which binds to more than one metal coordination site, to produce a complex which is more stable than those formed by monohydroxy compounds.

Suitable monohydroxy alcohols employable in formulation of the liquid admixture compositions employed in the process of the present invention include aliphatic alcohols of 1 to 12 carbon atoms, preferably 4 to 10 carbon atoms. Although the monohydroxy compound employable herein may be substituted with functional groups which are inert to the reactants present, for example, halo-, such as chloro or fluoro; nitro; cyano; carbonyl; and carboxyl, the readily available aliphatic monohydroxy-containing organic compounds containing only carbon, hydrogen and oxygen are particularly satisfactory for use in the present invention. Illustrative suitable monohydroxy compounds include methanol, ethanol, propanol, hexanol, 2-ethyl hexanol and particularly preferred is tertiary butyl alcohol. The monohydroxy alcohol proportion of the admixture is generally adjusted so that sufficient monohydroxy alcohol is introduced to provide the maximum concentration of molybdenum which is stable in accordance with the invention.

The polyhydroxy compounds suitable for use in formulation of the aforementioned admixture composition also may contain up to about 12 carbon atoms. Such polyhydroxy compounds may contain generally 2 to 4 hydroxyl groups, but preferably contain 2 hydroxyl groups, i.e., glycols or derivatives thereof, such as glycol ethers, provided these compounds contain at least one hydroxyl group. As is the case in connection with the monohydroxy alcohol referred to above, the polyhydroxy compounds may be substituted with functional groups which are inert to reactants present, but polyhydroxy compounds containing solely carbon, hydrogen and oxygen are particularly preferred. Typical illustrative polyhydroxy compounds employable in the process of the invention include ethylene glycol, propylene glycol, butylene glycols such as 1,4-butanediol, catechol and alkylene ethers of such glycols, including the methyl and ethyl ethers thereof. In general, the polyhydroxy alcohol is employed in an amount of at least 2 moles of polyhydroxy alcohol per mole of molybdenum to be solubilized, preferably between about 2 moles and 8 moles of polyhydroxy alcohol per mole of molybdenum to be solubilized. However, large excesses of polyhydroxy alcohol should be avoided since such compounds have a deleterious effect in subsequent epoxidations, and hence, large excesses are not favored for molybdenum solubilization.

The third component of the liquid composition employed for solubilization of the thermally precipitated molybdenum-containing solid comprises an oxidizing agent such as an organic peroxide and/or hydroperoxide. Typical illustrative organic peroxides and hydroperoxides employable herein include tertiary butyl hydroperoxide, ditertiary butyl peroxide, cumene hydroperoxide, ethylbenzene hydroperoxide, methyl tertiary butyl peroxide; preferred oxidizing agents include any organic hydroperoxide in which the peroxy group is bound directly to at least one tertiary carbon atom thereof. In general, the oxidizing agent is employed in an amount of at least about 3 and preferably between about 5 and 15 moles per mole of molybdenum to be solubilized.

The temperature employed to solubilize precipitated molybdenum solids may range between about 20° C. and about 130° C. and preferably between 50° C. and about 90° C. Temperatures lower than about 20° C. necessitate unduly long reaction times and are not favored. A particularly convenient temperature is the reflux temperature of the liquid admixture into which the molybdenum containing solids are being solubilized. In general, atmospheric pressure for the solubilization reaction is suitable. When the reaction is carried out at higher temperatures which would cause volatilization of the alcohol, however, sufficient pressure may be utilized to maintain the liquid phase; for example, if methanol is employed as the monohydroxy alcohol component of the admixture, use of temperatures higher than about 63° C. require that superatmospheric pressure be used to maintain the liquid state.

The time required to solubilize precipitated solids to a stable active solution is a function of both temperature and the nature and proportion of the components of the admixture. Generally, solubilization requires from about 0.5 to about 4 hours.

Solubilization has also been observed to be somewhat dependent on the proportion of precipitated solids to the admixture solubilizing liquid. Although molybdenum concentrations in solution of up to about 5%, by weight, and greater, may be attained by the process of the present invention, the preferred amount of molybdenum to be solubilized will range from about 0.5 to about 4 parts, by weight, per 100 parts by weight of the solubilizing liquid admixture. As higher levels of solids are present, the stability of the solution obtained may be adversely affected.

As above indicated, it is desirable to avoid adding excess hydroxyl containing compounds to the epoxidation reaction when solubilized regenerated molybdenum catalyst of the present invention is employed. Accordingly, after the solubilization of thermally precipitated solids, it may be desirable to concentrate the molybdenum in solution, particularly if substantial quantities of primary alcohol are employed in the dissolution reaction. This is conveniently achieved by distilling the solution to remove excess monohydroxy alcohol. While additional solubilizing agents other than those specifically mentioned hereinabove in connection with the liquid composition admixture are not required, optionally, other solubilizing compounds known to those skilled in the art may be employed. In addition, conventional, physical purfication procedures may be adopted as an extension of the process of the invention for purposes of effecting purification of the catalyst composition produced in accordance with this process; for example, prior to recycle of the active molybdenum soluble catalyst solution, this liquid may be subjected to filtration to remove any included undesired solid materials.

In order to illustrate practice of the invention, the following examples are provided. However, it is to be understood that the examples are merely illustrative and are not intended as being restricted of the invention herein disclosed and as defined by the next claims. Parts and percentages are by weight, and temperatures are in degrees Centigrade, unless otherwise specified.

EXAMPLE I

A spent catalyst stream from a commercial molybdenum catalyzed epoxidation of propylene, as described in Kollar, U.S. Pat. No. 3,351,635, was thermally treated according to the method set forth in Lemke U.S. Pat. No. 3,887,361 to precipitate dissolved molybdenum as a dark, blue solid. In accordance with this method, the residual organic effluent derived from the process of epoxidation of propylene was heated with about 7% by weight of tertiary butyl alcohol at a temperature ranging from 170° to 215° over a 3 hour period at a pressure building up to about 500 psig.

To regenerate the solid as a reusable soluble, stable molybdenum catalyst, 0.656 parts of the solid were reacted with 23 parts of methanol, 5 parts of a solution comprised of about 40% by weight tertiary butyl hydroperoxide in tertiary butyl alcohol and 4 parts of propylene glycol by heating the reactants together at 60° for 30 minutes. The reaction mixture was then filtered to remove the trace of solids which remained. The filtered solution was then concentrated by distillation to remove methanol and other low boiling materials. The resulting homogeneous solution remaining in the distillation pot had the following composition by weight:
47,500 ppm dissolved Mo
48.0% propylene glycol
42.2% t-butyl alcohol
3.9% methanol
0.4% tertiary butyl hydroperoxide
The concentrated solution was an active, stable catalyst suitable for reuse in epoxidation of propylene.

EXAMPLE II

A thermally precipitated molybdenum-containing solid was obtained according to the Lemke procedure from a spent catalyst solution from a commercial propylene epoxidation as in Example I. To regenerate that molybdenum-containing solid as a reuseable soluble molybdenum catalyst, 0.654 parts of the solid was reacted with 27.01 parts of tertiary butyl alcohol and 5.03 parts of a solution of about 40% by weight tertiary butyl hydroperoxide in tertiary butyl alcohol, by heating the reactants together at 75° for 2 hours. The solution obtained after reaction amounted to 32.5 parts and contained 6450 ppm of dissolved molybdenum. A small amount (0.078 parts) of solid remained undissolved and that solid contained 49.5% by weight molybdenum. Thus, 100% by weight of the original molybdenum charged was recovered and accounted for as solid or solution. Dissolved molybdenum amounted to 84% by weight of that charged. In addition, upon standing for periods of up to 4 hours at 90°, the dissolved solution began to precipitate substantial quantities of molybdenum indicating unstable character of the originally formed molybdenum solution.

EXAMPLE III

A thermally precipitated molybdenum-containing solid was obtained from a spent catalyst solution from a commercial propylene epoxidation as in Example I. To regenerate that molybdenum-containing solid as a reuseable soluble molybdenum catalyst, 0.655 parts of the solid was reacted with 27 parts of tertiary butyl alcohol (TBA), 5.0 parts of a solution oxidate comprised of about 40% by weight tertiary butyl hydroperoxide in tertiary butyl alcohol and 1.03 parts of reagent grade propylene glycol (MPG) by heating the reactants together at 90° for 2 hours. The solution obtained after reaction amounted to 33.56 parts and contained 7580 ppm of dissolved molybdenum. A small amount (0.031 parts) of solid remained undissolved. Dissolved molybdenum amounted to 96% by weight of that charged.

This Example shows that added glycol together with monohydroxy alcohol results in higher levels of molybdenum solubilization, as compared with the results obtained in Example II.

EXAMPLES IV–VIII

Employing the procedure of Example III, a number of timed dissolutions of thermally precipitated molybdenum containing solids were conducted. Example IV, illustrative of the process of the present invention, is compared with Comparative Example V–VIII, for stability. The recipe, temperature of reaction and parts per million (ppm) of solubilized molybdenum over a 4 hour period are set forth in Table I, below:

TABLE I

| Example | IV | V | VI | VII | VIII |
|---|---|---|---|---|---|
| Recipe: | | | | | |
| molybdenum-containing solid (parts) | .652 | .654 | .654 | .657 | .658 |
| tertiary butyl alcohol (parts) | 27.00 | 27.01 | 30.75 | 27.00 | 26.99 |
| oxidate, as in Example III, (parts) | 5.0 | 5.00 | 1.25 | 5.00 | 5.01 |
| alcohol (parts) | 1.02 (MPG) | .30 (MPG) | 1.04 (MPG) | none | 0.44 (methanol) |
| T (°C.) | 90 | 90 | 90 | 90 | 90 |
| ppm soluble[1] Mo @ t (hr) | | | | | |
| 0.5 | 6530 | 7540 | 5770* | 6150 | 6540 |
| 1.0 | 7050 | 7120 | 5530* | 4860 | 6000 |
| 1.5 | 7030 | 7240 | 4980* | 4170 | 4520 |
| 2.0 | 7100 | 6770 | 4820* | 3990 | 4250 |
| 2.5 | 7070 | 6420 | 4540* | 3120 | 3090 |
| 3.0 | 7650 | 6000 | 4150* | 2320 | 2350 |
| 3.5 | 7420 | 5300* | 4060* | 1550 | 1990 |
| 4.0 | 7360 | — | — | 1000* | 1550 |
| MAX.[2] | 7400 | 7580 | 7410 | 7690 | 7590 |

[1] The analyzed molybdenum content in parts per million for the centrate from the reaction sample taken at the indicated time (in hours).
[2] The maximum value for the ppm soluble molybdenum, assuming complete solids dissolution and no loss of any reaction component.
*Indicates a change in solution color from yellow to deep green or blue, an indication of the complete consumption of the tertiary butyl hydroperoxide in the mixture.

As is apparent from the results set forth in Table I, above, rapid dissolution of molybdenum occurred in all cases, but stability of the catalyst solution over the indicated period was achieved only when the thermally precipitated molybdenum-containing solid was contacted with the admixture comprised of a monohydroxy alcohol, a polyhydroxy alcohol and an organic hydroperoxide when the polyhydroxy alcohol and organic hydroperoxide were present in at least certain minimum concentrations.

EXAMPLE IX

A thermally precipiated molybdenum-containing solid was obtained from a spent catalyst solution from a commercial propylene epoxidation as in Example I. To regenerate that molybdenum-containing solid as a reuseable soluble molybdenum catalyst, 0.654 parts of the solid was reacted with 26 parts of methanol, 5 parts of a solution of about 40% by weight tertiary butyl hydroperoxide in tertiary butyl alcohol and 1.0 part of propylene glycol by heating the reactants together at 60° for 30 minutes. The solution obtained after reaction amounted to 33.05 parts and contained 8700 ppm of dissolved molybdenum. A small amount (0.005 parts) of solid remained undissolved. Dissolved molybdenum amounted to greater than 99% by weight of that charged.

A stainless steel autoclave is charged with 70 parts propylene and heated to 130°. At that point, there is added to the reactor a mixture of 20 parts of tertiary butyl hydroperoxide (TBHP) and 50 parts of tertiary butyl alcohol which contains 100 ppm molybdenum from the solution obtained above. After 60 minutes, reaction at 130°, the mixture is quenched and analyzed for propylene oxides (PO) and unreacted tertiary butyl hydroperoxide. The TBHP reacted amounts to 93% of that charged, and PO is produced in 88% selectivity versus hydroperoxide reacted.

What is claimed is:

1. The process of regenerating a soluble molybdenum eomposition to obtain a stable catalyst solution capable of being employed as a catalyst in the process for the epoxidation of an olefin with an organic hydroperoxide which comprises thermally precipitating and separating a molybdenum-containing solid containing up to about 50 percent by weight, of molybdenum from a spent catalyst solution derived from a molybdenum-catalyzed olefin epoxidation reaction, said molybdenum-containing solid having been obtained by heating said spent catalyst solution with either (a) from about 0.5 to about 10 percent by weight, of water at a temperature of between about 150° C. and 250° C. under pressure or, (b) from about 5 to about 50 percent, by weight, of tertiary butyl alcohol, at a temperature of between about 100° C. and 300° C. in a closed vessel or under reflux, separating said thermally precipitated solid solubilizaing said separated precipitated solid to form a soluble molybdenum composition by contacting at a temperature of between about 20° C. and about 130° C. with an admixture comprising a monohydroxy alcohol, a polydroxy alcohol and an organic peroxide, said polyhydroxy alcohol being present in an amount of between about 2 moles and 8 moles per mole of molybdenum to be solubilized, and removing any undesired solid material remaining wtih the said solubilized molybdenum composition.

2. The process of claim 1 wherein said organic peroxide is present in an amount of at least 3 percent by weight, based on the weight of said admixture.

3. The process of claim 1 wherein said organic peroxide is present in an amount of at least about 5 but not more than 15 moles per mole of molybdenum to be solubilized.

4. The process of claim 1 wherein said organic peroxide contains a peroxy group which is bound directly to at least one tertiary carbon atom.

5. The process of claim 1 wherein said monohydroxy alcohol is a teritiary alcohol containing of from about 4 to 10 carbon atoms, said polyhydroxy alcohol is a glycol containing of from 2 to 6 carbon atoms and is present in an amount of between about 4 and 8 moles per mole of molybdenum to be solubilized, said peroxy compound is an organic peroxide contains peroxy group which is bound directly to at least one tertiary carbon atom, and is present in an amount of between about 5 and 15 moles per mole of molybdenum to be solubilized, and said contacting is effected at a temperature of between about 50° C. and about 90° C.

6. The process of claim 5 wherein removal of any remaining solid materials is effected by filtration.

7. The process of claim 1 wherein contacting of the said precipitated solid is effected at a temperature of between about 50° C. and 90° C. with an admixture comprising tertiary butyl alcohol, propylene glycol, present in an amount of between about 2 and 8 moles per mole of molybdenum to be solubilized, and teritiary butyl hydroperoxide, present in an amount between about 5 and 15 moles per mole of molybdenum to be solubilized.

8. The process of claim 7 wherein said thermally precipitated molybdenum-containing solid is obtained by admixing said spend catalyst stream with water, in an amount between about 0.5 and 10 percent, based on the weight of the spend catalyst stream, to form an admixture of the spent catalyst stream and water, and heating said admixture to a temperature in the range of about 150° C. to about 250° C. under pressure sufficient to maintain said admixture in the liquid phase and for a time sufficient to precipitate at least a portion of the molybdenum contained in said admixture as a thermally precipitated solid.

9. The process of claim 7 wherein said thermally precipitated molybdenum-containing solid is obtained by heating said spent catalyst solution with from about 5 to about 50 percent by weight of tertiary butyl alcohol to a temperature of between about 100° C. to 300° C. in a closed vessel or under reflux.

* * * * *